(12) United States Patent
Siegel et al.

(10) Patent No.: US 8,845,514 B2
(45) Date of Patent: Sep. 30, 2014

(54) MALE URETHRAL PROSTHESIS WITH TENSIONING MEMBER

(75) Inventors: Steven W. Siegel, North Oaks, MN (US);
Kevin R. Arnal, Chanhassen, MN (US);
Robert E. Lund, St. Michael, MN (US);
Kimberly A. Anderson, Eagan, MN
(US); Brian P. Watschke, Eden Prairie,
MN (US)

(73) Assignee: AMS Research Corporation,
Minnetonka, MN (US)

( * ) Notice: Subject to any disclaimer, the term of this patent is extended or adjusted under 35 U.S.C. 154(b) by 497 days.

(21) Appl. No.: 13/171,738

(22) Filed: Jun. 29, 2011

(65) Prior Publication Data

US 2011/0257471 A1 Oct. 20, 2011

Related U.S. Application Data

(63) Continuation of application No. 12/789,614, filed on May 28, 2010, now Pat. No. 7,998,055, which is a continuation of application No. 10/923,914, filed on Aug. 23, 2004, now Pat. No. 7,753,839, which is a continuation of application No. 10/422,626, filed on Apr. 24, 2003, now Pat. No. 7,198,597.

(60) Provisional application No. 60/378,602, filed on May 7, 2002, provisional application No. 60/429,341, filed on Nov. 26, 2002.

(51) Int. Cl.
*A61F 2/02* (2006.01)
*A61F 2/00* (2006.01)

(52) U.S. Cl.
CPC ....... *A61F 2/0045* (2013.01); *A61F 2250/0078* (2013.01)

USPC ............................................. 600/37

(58) Field of Classification Search
USPC ..................... 600/29–32, 37; 128/897, 898
See application file for complete search history.

(56) References Cited

U.S. PATENT DOCUMENTS

| 3,054,406 A | 9/1962 | Usher |
| 3,789,828 A | 2/1974 | Schulte |
| 4,019,499 A | 4/1977 | Fitzgerald |

(Continued)

FOREIGN PATENT DOCUMENTS

| DE | 19511998 | 10/1996 |
| EP | 0409592 | 1/1991 |

(Continued)

OTHER PUBLICATIONS

Mulcahy, John J., "Tips for Successful Placement of the Artificial Urinary Sphincter", Contemporary Urology, Sep. 1999, pp. 1-5.

(Continued)

*Primary Examiner* — Samuel Gilbert
(74) *Attorney, Agent, or Firm* — Kagan Binder, PLLC (57) ABSTRACT

The present invention provides a urethral prosthesis including a first and a second arm that join to form a junction, and a stem that is also joined to the junction. The junction is adapted to exert sufficient pressure on a portion of a patient's urethra to prevent unintentional voiding of the patient's bladder. However, upon exerting a tension force on the stem, the pressure exerted by the junction is reduced such that the patient's bladder may be intentionally voided.

20 Claims, 9 Drawing Sheets

(56) References Cited

U.S. PATENT DOCUMENTS

| | | | |
|---|---|---|---|
| 4,386,601 A | 6/1983 | Trick | |
| 4,452,245 A | 6/1984 | Usher | |
| 4,552,128 A | 11/1985 | Haber | |
| 4,587,954 A | 5/1986 | Haber | |
| 4,682,583 A | 7/1987 | Burton et al. | |
| 4,878,889 A | 11/1989 | Polyak | |
| 4,994,019 A | 2/1991 | Fernandez et al. | |
| 4,994,020 A | 2/1991 | Polyak | |
| 5,041,128 A | 8/1991 | Korthoff | |
| 5,163,897 A | 11/1992 | Persky | |
| 5,292,328 A | 3/1994 | Hain et al. | |
| 5,520,606 A | 5/1996 | Schoolman et al. | |
| 5,785,640 A | 7/1998 | Kresch et al. | |
| 5,840,011 A | 11/1998 | Landgrebe et al. | |
| 5,934,283 A | 8/1999 | Willem et al. | |
| 6,042,534 A * | 3/2000 | Gellman et al. | 600/30 |
| 6,117,067 A | 9/2000 | Gil-Vernet | |
| 6,258,098 B1 | 7/2001 | Taylor et al. | |
| 6,319,264 B1 | 11/2001 | Tormiilii et al. | |
| 6,382,214 B1 | 5/2002 | Raz et al. | |
| 6,406,423 B1 | 6/2002 | Scetbon | |
| 6,425,924 B1 | 7/2002 | Rousseau | |
| 6,502,578 B2 | 1/2003 | Raz et al. | |
| 6,506,190 B1 | 1/2003 | Walshe | |
| 6,575,897 B1 | 6/2003 | Orv et al. | |
| 6,579,225 B2 | 6/2003 | Pregenzer et al. | |
| 6,592,515 B2 * | 7/2003 | Thierfelder et al. | 600/37 |
| 6,612,977 B2 | 9/2003 | Staskin et al. | |
| 6,638,210 B2 | 10/2003 | Berger | |
| 6,648,921 B2 | 11/2003 | Anderson et al. | |
| 6,652,450 B2 * | 11/2003 | Neisz et al. | 600/30 |
| 6,755,781 B2 | 6/2004 | Gellman | |
| 6,802,807 B2 | 10/2004 | Anderson et al. | |
| 6,911,002 B2 | 6/2005 | Fierro | |
| 2002/0028980 A1 | 3/2002 | Thierfelder et al. | |
| 2002/0107525 A1 | 8/2002 | Harari et al. | |
| 2002/0116018 A1 | 8/2002 | Stevens et al. | |
| 2002/0128670 A1 | 9/2002 | Ulmsten et al. | |
| 2002/0147382 A1 | 10/2002 | Neisz et al. | |
| 2002/0156487 A1 | 10/2002 | Gellman et al. | |
| 2002/0161382 A1 | 10/2002 | Neisz et al. | |
| 2003/0065402 A1 | 4/2003 | Anderson et al. | |
| 2003/0130670 A1 | 7/2003 | Anderson et al. | |
| 2003/0220538 A1 | 11/2003 | Jacquetin | |

FOREIGN PATENT DOCUMENTS

| | | |
|---|---|---|
| EP | 0650703 | 5/1995 |
| FR | 2824257 | 11/2002 |
| WO | WO 00/18319 | 4/2000 |
| WO | WO 00/27304 | 5/2000 |
| WO | WO 00/74633 | 12/2000 |
| WO | WO 0106951 | 2/2001 |
| WO | WO 0145588 | 6/2001 |
| WO | WO 0145589 | 6/2001 |
| WO | WO 02/058563 | 8/2002 |
| WO | WO 02/062237 | 8/2002 |
| WO | WO 02/089704 | 11/2002 |
| WO | WO 2004/016196 | 2/2004 |

OTHER PUBLICATIONS

Daher, N. et al., "Pre-pubic TVT: An alternative to classic TVT in selected patients with urinary stress incontinence," European Journal of Obstetrics & Gynecology and & Reproductive Biology, vol. 107, p. 205-207 (2003).

Petrou, S.P. et al., "Artificial Urethral Sphincter for Incontinence," Urology 56, pp. 353-359, 2000.

Product Sheet "InVance" Male Sling System, American Medical Systems, Inc., 4 pages, 2001.

* cited by examiner

MALE URETHRAL PROSTHESIS WITH TENSIONING MEMBER

REFERENCE TO RELATED APPLICATIONS

The present application is a continuation of U.S. patent application Ser. No. 12/789,614, filed May 28, 2010 now U.S. Pat. No. 7,998,055, entitled Male Urethral Prosthesis with Tensioning Member," which is a continuation of U.S. patent application Ser. No. 10/923,914, filed Aug. 23, 2004 (now U.S. Pat. No. 7,753,839) entitled "Male Urethral Prosthesis with Tensioning Member," which is a continuation of U.S. patent application Ser. No. 10/422,626 filed Apr. 24, 2003 (now U.S. Pat. No. 7,198,597) entitled "Male Urethral Prosthesis With Tensioning Member," which claims the benefit of U.S. Provisional Patent Application No. 60/378,602 filed May 7, 2002, and U.S. Provisional Patent Application No. 60/429,341 filed Nov. 26, 2002. All of the aforementioned applications are hereby incorporated by reference in their entireties.

BACKGROUND OF THE INVENTION

Urinary incontinence is a condition characterized by involuntary loss of urine beyond the individual's control. One cause for this loss of control is damage to the urethral sphincter caused by, for example, prostatectomy, radiation therapy or pelvic accidents. Other causes of incontinence include bladder instability, over-flowing incontinence and fistulas.

Currently, there are a few known surgical treatments for male incontinence, including the implantation of an Artificial Urinary Sphincter (e.g. AMS Sphincter 800 available from American Medical Systems, Minnetonka, Minn.), the implantation of a bone-screw fixated male sling (e.g. AMS InVance, available from American Medical Systems), and a few other procedures. Other procedures that have been largely discontinued include the implantation of a Kaufman III Prosthesis beneath the urethra. All of these prostheses exert a pressure on the urethra to prevent unintentional voiding of the bladder.

A drawback to these aforementioned techniques relates to tensioning. After implantation of the InVance male sling, for example, any adjustments to the pressure exerted on the urethra by the prosthesis must be performed during a separate procedure. To adjust the Artificial Urinary Sphincter, additional instrumentation may also be required. These additional procedures may subject the patient to increased risk of infection and may also make the procedure more costly. An additional drawback is that these devices have little tolerance for improvement or deterioration in the patient's incontinence condition. Thus, minor changes in the patient's condition may require another surgical procedure.

SUMMARY OF THE INVENTION

In one embodiment, the present invention provides a urethral prosthesis including a first arm, a second arm and a stem. The first and second arms meet or join to define a junction that is adapted to exert sufficient pressure on a portion of a patient's urethra to prevent unintentional voiding of a patient's bladder. The stem is joined to the junction such that a tension force may be exerted on the stem to reduce the pressure exerted on the portion of the patient's urethra by the junction such that the patient's bladder may be voided. The urethral prosthesis may further include a tensioning member associated with the first arm, second arm and/or stem, which may be adapted to facilitate manipulation of the urethral prosthesis during implantation in a patient.

In another embodiment, the present invention provides a method of treating urinary incontinence, in which a prosthesis as described herein is implanted into a patient. The first and second arms may be internally oriented in a variety of manners. For example, the first and second arms may be oriented or positioned anterior, posterior or transobturator relative to the patient's pubic symphysis. The junction contacts a portion of the urethra and exerts a sufficient pressure to prevent unintentional voiding of the patient's bladder. The stem may be positioned or implanted in the patient's scrotum to facilitate easy patient access. When manual tension is placed on the stem, the pressure exerted on the portion of the urethra by the junction decreases such that the patient's bladder may be intentionally voided. After voiding, the tension may be released such that the junction once again exerts sufficient pressure on the portion of the urethra to prevent unintentional voiding of the patient's bladder. Advantageously; the urethral prosthesis oldie present invention may be secured by tissue in-growth and/or tissue encapsulation of portions of the prosthesis.

DETAILED DESCRIPTION

Figure 1:
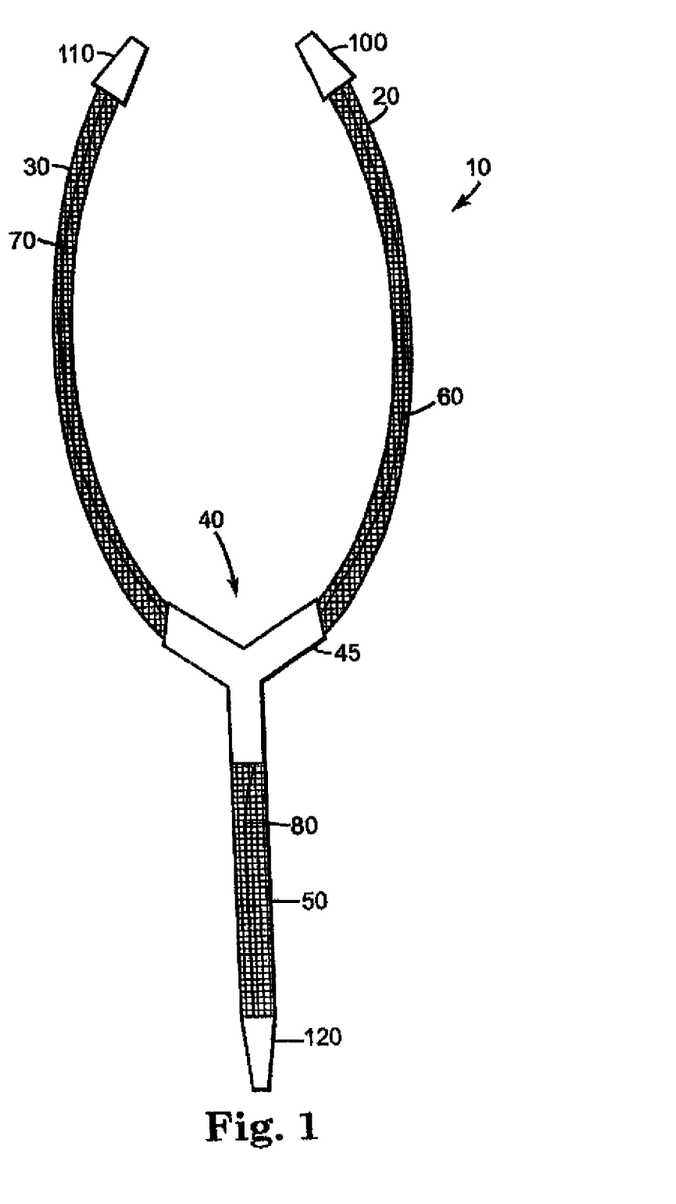
FIG. 1 schematically illustrates a perspective view of an embodiment of the present invention.
Figure 2:
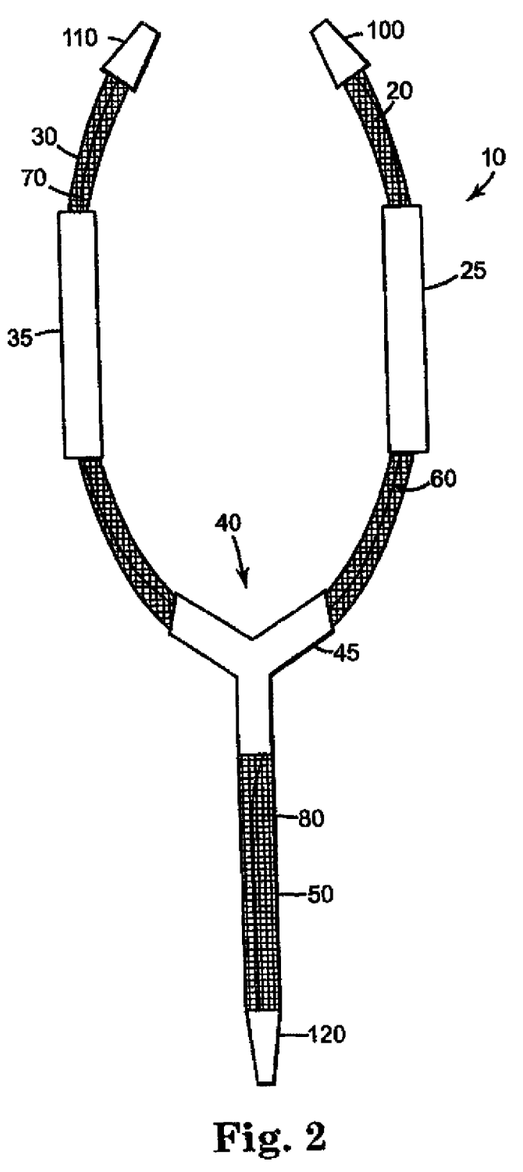
FIG. 2 schematically illustrates a perspective view of an embodiment of the present invention.
Figure 3:
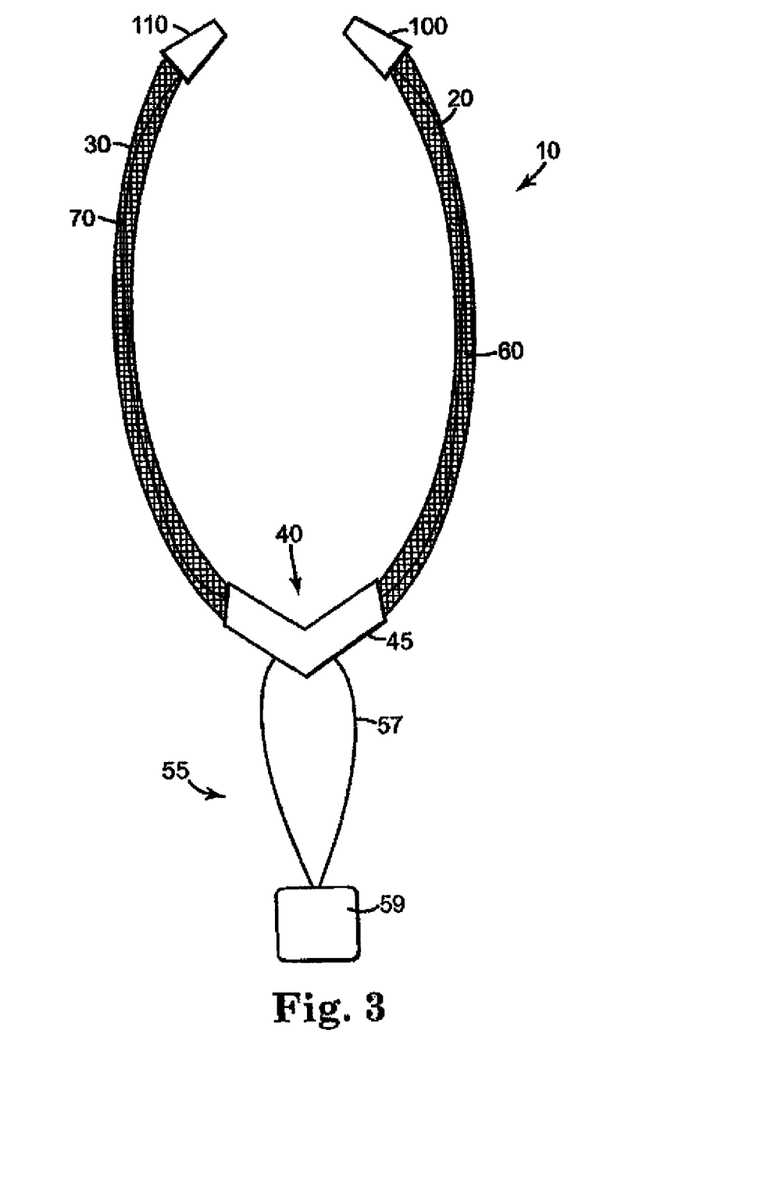
FIG. 3 schematically illustrates a perspective view of an embodiment of the present invention.

FIGS. 1-3 illustrate a urethral prosthesis 10 according to various embodiments of the present invention. Urethral prosthesis 10 includes a first arm 20 and a second arm 30 that join to form a junction 40. A stem 50 is further joined to the junction 40.

A wide range of suitable materials or combinations of suitable materials may be used to form the first and second arms 20, 30. The first and second arms 20, 30 in the illustrated embodiment may include one or more lengths of flexible, longitudinally extendable material. The material may be inelastic or elastic, longitudinally extendable or non-extendable, and may be patterned, for example in a mesh pattern, which may encourage tissue in-growth.

Suitable materials for the first and second arms 20, 30 may include, but are not limited to materials such as polyester, polypropylene, nylon, polyethylene terephthalate, polytetrafluorethylene, expanded polytetrafluoroethylene, polyvinylidene fluoride, polyamide and silk, as well as derivatives, combinations and hybrids of these materials. Preferably, at least the end portions of the first and second arms 20, 30 may be configured, for example as a mesh, to promote tissue in-growth. Alternatively, the first and second arms 20, 30 may be at least partially formed from a bioabsorbable material such as polylactic acid or polyglycolic acid. Suitable materials are also reported in U.S. Published Patent Application No. 2002/0147382. Still further, the urethral prosthesis 10 may be coated with a suitable bioactive material having a desired physiological effect. For example, suitable bioactive materials may be selectively coated on desired areas or portions of the urethral prosthesis 10 to reduce inflammation, encourage tissue in-growth and/or to prevent infection in specific areas of a patient.

In one embodiment, the first and second arms 20, 30 include portions having a polymeric mesh coated with a silicone material or other suitable material, including but not limited to an elastomer, polypropylene, polyester, polyurethane, polyamide, or a derivative, combination or hybrid thereof. In an alternate embodiment, portions of the first and second arms 20, 30 may include an additional coating or tubing. For example, in the embodiment illustrated in FIG. 2, tubes 25, 35 encompass or surround portions of the first and second arms 20, 30. Tubes 25, 35 may be used, for example, when the first and second arms 20, 30 are formed from a longitudinally extensible mesh. The tubes 25, 35 may allow longitudinal extension of the mesh within the tube independent of the mesh outside of the tube. Suitable materials for the tubes 25, 35 may include, but are not limited to polypropylene, nylon, polyester, polytetrafluoroethylene, polyvinyl chloride, polyamide, and derivatives, combinations and hybrids thereof.

The first and second arms 20, 30 may be formed from discrete lengths of materials, which are attached or joined at respective proximal ends by a variety of suitable methods to form the junction 40. Alternatively, the first and second arms 20, 30 may be formed from a single length of material such that the junction 40 is formed approximately at a center point of the length of material that forms the first and second arms 20, 30.

The first and second arms 20, 30 may be sized and shaped for internal implantation and attachment in the vicinity of a patient's pubic symphysis, as reported in further detail below. In one embodiment, the arms 20, 30 may each have a length between about 5 and about 30 cm, more particularly between about 15 and about 25 cm. The arms 20, 30 may have a width of between about 0.5 and about 5 cm, more particularly between about 0.5 cm and about 2.5 cm. Additionally, the width of the first and second arms 20, 30 may not be uniform.

The first and second arms 20, 30 join to form the junction 40. The junction 40 is adapted to exert sufficient pressure on a patient's urethra to prevent unintentional voiding. The junction 40 may include portions that are wider than the first and second arms 20, 30. For example, the junction 40 may have a portion between about 3 and about 5 cm long and between about 1 and about 2 cm wide that is adapted to exert a force against a patient's urethra when implanted. In one embodiment, the junction includes a coating or overcoat 45 covering proximal portions of first and second arms 20, 30. In embodiments in which the first and second arms 20, 30 are formed from discrete lengths of material, the overcoat 45 may function to secure the first and second arms 20, 30 together. The overcoat 45 of the junction may extend between about 1 and about 5 cm along the first and second arms 20, 30, more particularly between about 1 and about 3 cm. The overcoat 45 may have a thickness of between about 0.15 mm and about 3 mm, more particularly between about 0.5 mm and about 1.5 mm. Suitable overcoat materials include, but are not limited to, polymeric materials such as elastomers, silicones, polypropylenes, polyesters, polyurethanes, polyvinyl chlorides, polyamides and derivatives, combinations and hybrids thereof. The overcoat 45 may discourage tissue in-growth in the vicinity of the patient's urethra, while allowing tissue encapsulation. Tissue encapsulation may allow some degree of movement of the junction 40.

In an alternate embodiment, the junction 40 may include a compression member (not shown) secured to the first and second arms. The compression member may include a rigid or flexible material that is adapted to exert pressure against a portion of a patient's urethra to prevent unintentional voiding of the patient's bladder. For example, the compression member may include a resilient pillow or pouch positioned to exert a pressure against a portion of a patient's urethra.

Stem 50 is joined to the first and second arms 20, 30 at the junction 40. The stem 50 may be formed from the same types of materials as the first and second arms 20, 30. However, the stem 50 is generally formed from a material that has low elasticity such that the stem 50 does not significantly stretch upon the exertion of a tension force.

The stem 50 may be formed from a discrete length of material, or may be formed from a single length of material including the first arm 20 and/or second arm 30 of the prosthesis 10. A portion of the stem 50 may also include the overcoat 45 formed at the junction 40. For example, the overcoat 45 may extend between about 0.25 and about 3 cm, more particularly between about 0.5 and about 1 cm along a proximal portion of the stem. In embodiments in which the first and/or second arms 20, 30 and the stem 50 include discrete lengths of material, the overcoat 45 may attach or join the discrete lengths of material together at the junction 40.

In an alternate embodiment illustrated in FIG. 3, a stem 55 may include a filament 57 and a tab 59. The filament should be capable of withstanding the exertion of a tension force on the tab 59.

The urethral prosthesis 10 of the present invention may also include one or more tensioning members 60, 70, 80, which are associated with the urethral prosthesis. The one or more tensioning members 60, 70, 80 may be secured to one or both of the first and second arms 20, 30 and may also be optionally secured to the stein 50. As described in greater detail below, the tensioning member generally functions to provide uniform movement of the urethral prosthesis 10, particularly the first and second arms 20, 30 during implantation in a patient such that suitable pressure is exerted on a patient's urethra by the junction 40.

In one embodiment, the tensioning member includes at least one filament. In the embodiment illustrated in FIGS. 1 and 2, the tensioning member 60, 70, 80 includes a first filament 60 secured to the first arm 20, a second filament 70 secured to the second arm 30 and a third filament 80 secured to the stem 50. More particularly, each filament may be independently secured to a distal end of the first arm 20, second arm 30 and/or the stem 50. Each filament may also be secured at a proximal end of the first arm 20, second arm 30, and/or stem 50, as well as the junction 40. In one embodiment, the first, second and third filaments 60, 70, 80 are secured to at least one of the other filaments 60, 70, 80 at the junction 40. In another embodiment, the first, second and third filaments 60, 70, 80 are secured to dilators 100, 110, 120.

One or more dilators 100, 110 and 120 may be secured to the distal ends of the first and second arms 20, 30 and/or the stem 50 to facilitate implantation in a patient. More particularly, the dilators 100, 110 and 120 may associate the urethral prosthesis 10 to a guide needle, which may be used to position and/or orient the urethral prosthesis 10, as reported in greater detail below.

The urethral prosthesis 10 may be implanted in a patient by a variety of suitable methods. In one embodiment, a small transverse scrotal incision and one or two small horizontal suprapubic incisions are made. A suitable guide needle, similar to the needles reported in U.S. Published Patent Application Nos. 2002/0147382, 2002/0099259 A1, 2002/0099258 A1 and/or 2001/0161382 may be inserted into the first suprapubic incision and passed either anterior or superior to the pubic symphysis and towards the scrotal incision. Once a first guide needle has been successfully guided and/or positioned, a second guide needle may be inserted through the optional second suprapubic incision and positioned and/or guided in a similar manner, in opposition to the first needle. The distal ends of the guide needles may then be secured to the dilators 100 and 110, and the urethral prosthesis 10 may be pulled up through the suprapubic incisions. A third guide needle may be used to insert the stem 50 into the scrotal incision and to guide the stem 50 into the proper location and orientation within the scrotum. For example, the stem 50 may be positioned at the posterior scrotal midline of the patient. During the implantation procedure, the first and second arms 20, 30 and/or the stem 50 may be covered with heat sealed plastic sheaths (not shown), which are removed prior to completing the procedure. In one embodiment, the sheath is heat sealed to first and second arms 20, 30 and stem 50, and the plastic sheath forms the connection to the connectors 100, 110 and 120.

The urethral prosthesis 10 may then be positioned in the vicinity of a patient's descending rami of the pubic bone such that the junction 40 contacts a portion of the patient's urethra. The pressure exerted on the urethra may be adjusted during implantation. For example, the pressure may be increased by pulling on the distal ends of the first and second arms 20, 30 until a sufficient force is exerted on the urethra. Alternatively, the pressure may be reduced by exerting downward tension on the junction 40 or the stem 50. The tensioning members 60, 70, 80 may facilitate these tension adjustments to the urethral prosthesis by allowing the prosthesis to be manipulated in a uniform fashion, rather than by having certain portions of the prosthesis move while other portions remain immobile. The tensioning members may be removed prior to completing the implantation procedure, or may remain secured to the urethral prosthesis substantially permanently. In one embodiment, the junction 40 exerts a pressure between about 50 and about 300 cm, $H_2O$, more particularly, between about 50 and about 140 cm $H_2O$, even more particularly, between about 50 and about 70 cm $H_2O$ on the patient's urethra. Advantageously, the exerted pressure may be higher than in conventional prostheses because the pressure may be released by exerting tension on the stem as reported in greater detail below.

The urethral prosthesis 10 may be secured internally within the patient in a variety of suitable manners. In one embodiment, the urethral prosthesis 10 may be secured solely by tissue in-growth and/or tissue encapsulation. More specifically, portions of the first and second arms, 20, 30 and/or the stem 50 may be configured, for example, in a mesh configuration, to encourage tissue in-growth. Other portions, including the junction 50 and/or portions of the first and second arms, may be configured in a manner that does not promote tissue in-growth, but allows for tissue encapsulation. During the weeks and months after implantation, portions of the urethral prosthesis 10 may become increasingly secured within the patient by tissue in-growth and/or tissue encapsulation. In this manner, portions that are in-grown with tissue secure the urethral prosthesis 10, while portions that are encapsulated in tissue allow for some movement of portions of the urethral prosthesis 10 during use. Advantageously, this embodiment does not require (but may include) additional bone or soft tissue anchors to further secure the urethral prosthesis 10.

In an alternate embodiment, the first and second arms may be secured to a soft tissue region, such as at the obturator internus muscles or the gracilis muscles, with a combination of suitable soft tissue anchors and sutures. In an additional embodiment, a combination of tissue in-grown portions and suitable anchors may secure the urethral prosthesis 10. In yet another embodiment, as in U.S. Published Patent Application No. 2002/10752, the first and second arms 20, 30 may be secured to a suitable portion of the patient's descending rami by a combination of anchors and sutures as reported.

In yet another embodiment, the urethral prosthesis 10 may be secured to the pelvic origin of the gracilis tendon. For example, a tissue anchor may be implanted in the most proximal position to the inferior pubic ramus, where the gracilis tendon attaches to the bone. After the tissue anchor is inserted lateral to the tendon, a suture may be passed medial through the tendon to secure the prosthesis in place. This technique may be used on both sides of the body in opposition to secure the urethral prosthesis 10. A variety of suitable tissue anchor designs and materials may be used for securing the urethral prosthesis 10 in this embodiment. In one embodiment, for example, a "T" shaped tissue anchor may be formed from titanium, plastic, or stainless steel and may be deployed with a suitable deployment tool and attached to a suture to secure the sling to the tissue.

In an alternate embodiment, one or more tissue anchors may be used to secure the urethral prosthesis to the obturator internus muscles. The anchor may be deployed through the obturator foramen and pass through the obturator externus muscle to the obturator internus muscle. The anchor may then be positioned in the anterior recess of the ischio-anal fossa, just anterior to the obturator internus muscle. At least one anchor in each obturator internus muscle in opposition may be used to secure the sling in place. In a further embodiment, the urethral prosthesis 10 may be secured in this position by screwing a bone screw proximal to the gracilis tendon into the inferior pubic ramus. Alternatively, the urethral prosthesis may be secured to the superior or inferior pubic rami with a bone screw.

Figure 4A:
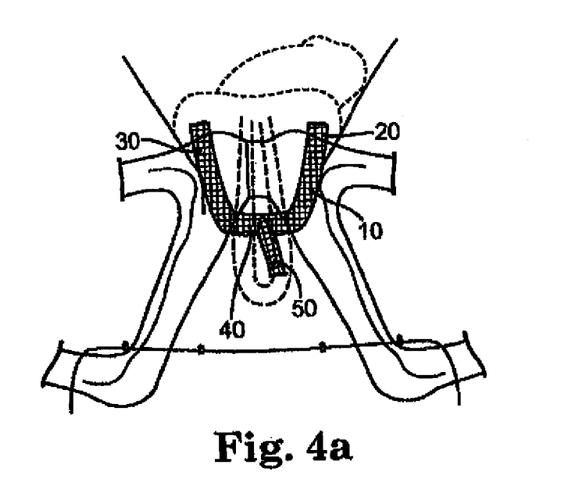
FIGS. 4a-b illustrate an implanted prosthesis according to an embodiment of the present invention.
Figure 4B:
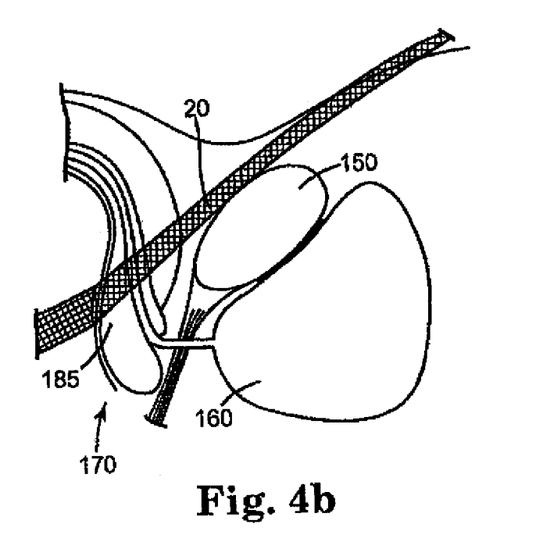
Figure 5A:
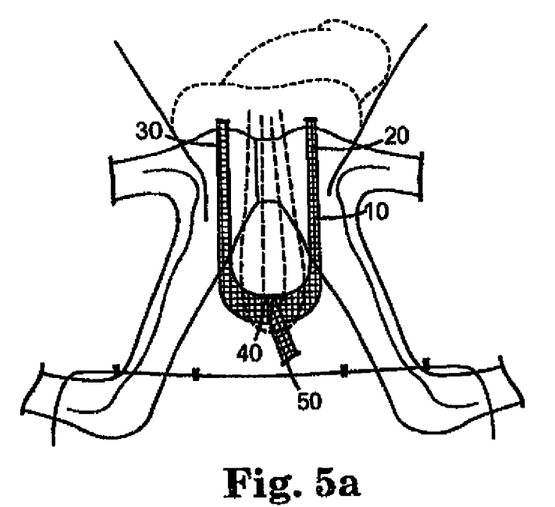
FIGS. 5a-b illustrate an implanted prosthesis according to an embodiment of the present invention.
Figure 5B:
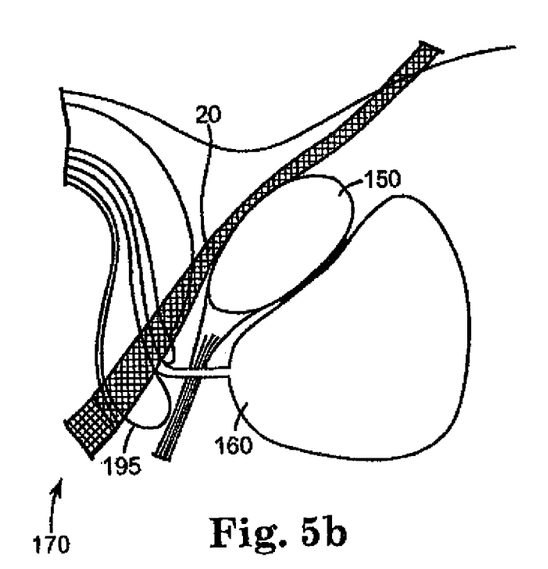

FIGS. 4-9 illustrate several implantation orientations for the urethral prosthesis 10. FIGS. 4 and 5 illustrate an anterior pubic symphysis orientation, in which the first and second arms 20, 30 extend anterior to the pubic symphysis 150. This orientation may be beneficial because of the reduced chance of causing vascular, neural or visceral damage during implantation. In FIGS. 4*a-b*, the junction 40 is positioned to exert pressure on a proximal portion 185 of the patient's urethra 170. In FIGS. 5*a-b*, the junction 40 is positioned to exert pressure on a distal portion 195 of the patient's urethra 170.

Figure 6A:
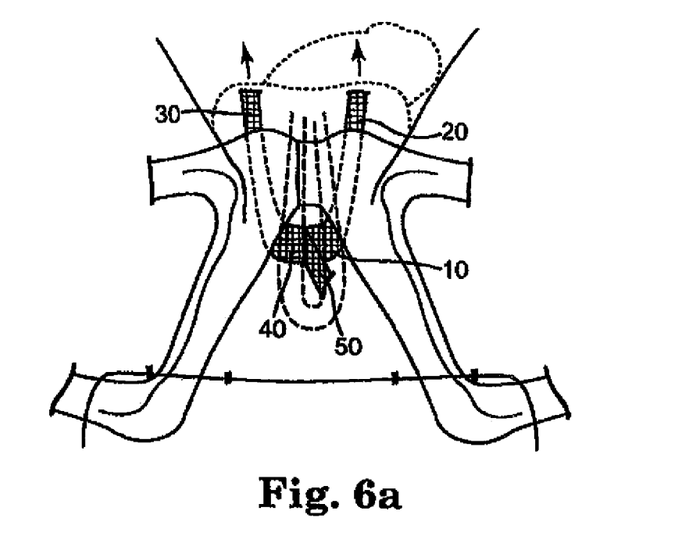
FIGS. 6a-b illustrate an implanted prosthesis according to an embodiment of the present invention.
Figure 6B:
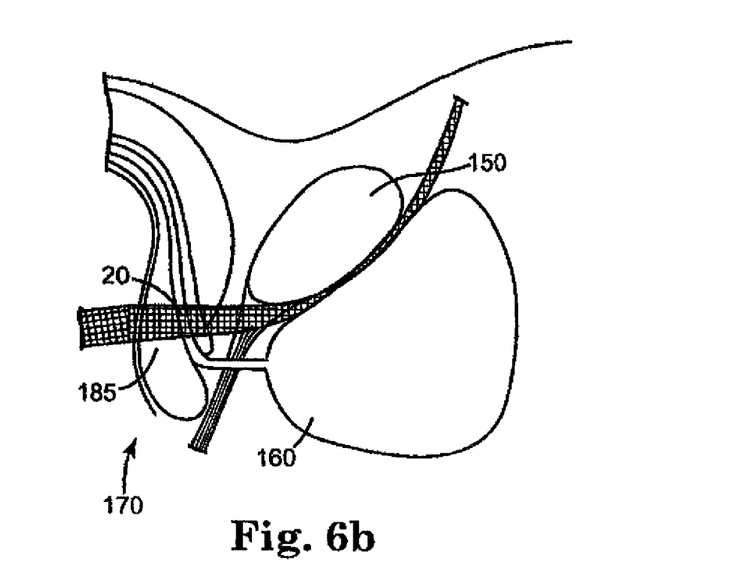
Figure 7A:
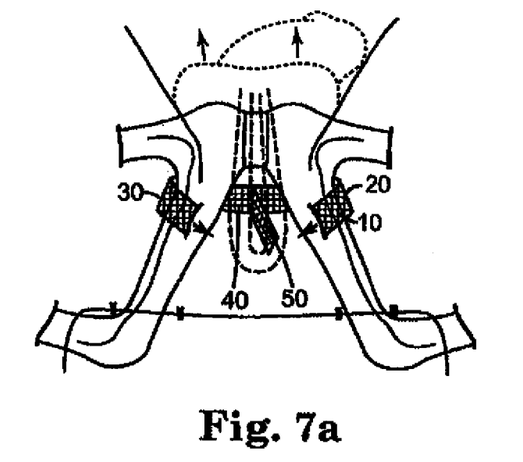
FIGS. 7a-b illustrate an implanted prosthesis according to an embodiment of the present invention.
Figure 7B:
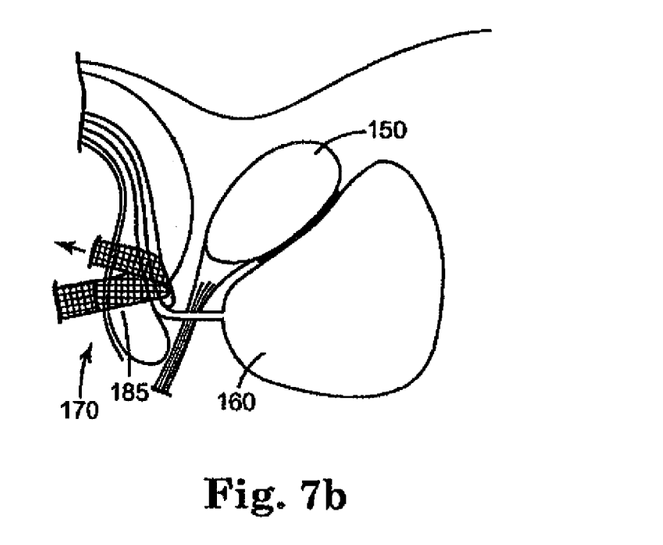
Figure 8A:
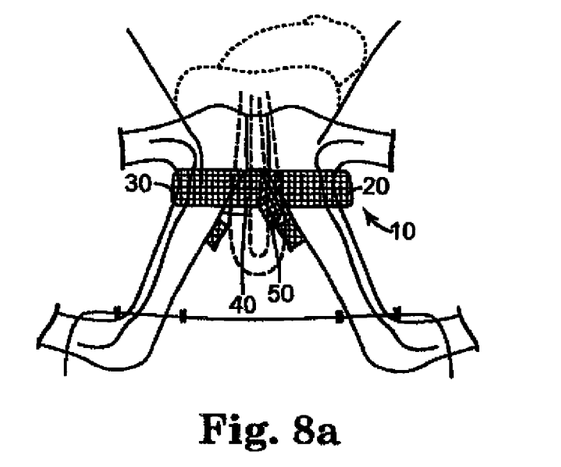
FIGS. 8a-b illustrate an implanted prosthesis according to an embodiment of the present invention.
Figure 8B:
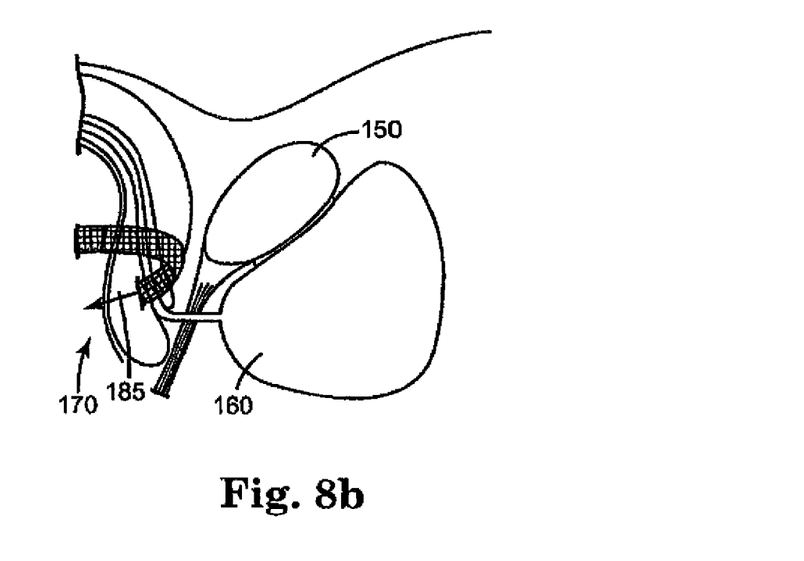
Figure 9A:
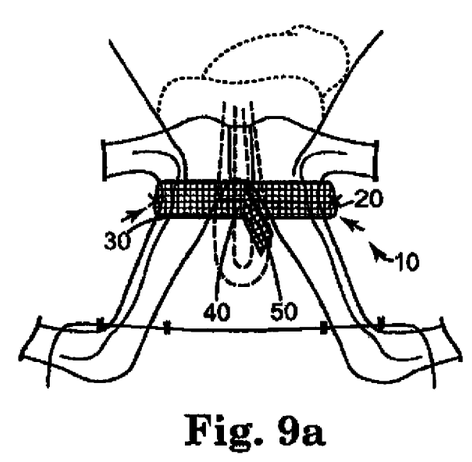
FIGS. 9a-b illustrate an implanted prosthesis according to an embodiment of the present invention.
Figure 9B:
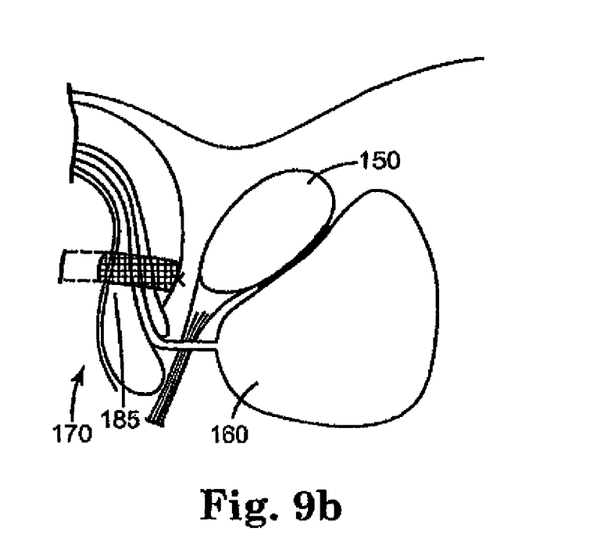

FIGS. 6*a-b* illustrate a posterior pubic symphysis orientation, in which first and second arms 20, 30 extend posterior to the pubic symphysis 150. In this orientation, the junction 40 exerts pressure on the proximal portion 185 of the patient's urethra 170. FIGS. 7*a-b*, 8*a-b* and 9*a-b* illustrate various transobturator orientations, in which the first and second arms 29, 30 extend around the pubic rami.

After implantation, the prosthesis of the present invention exerts sufficient force upon a portion of the patient's urethra to prevent unintentional voiding of the patient's bladder. However, when a sufficient tension force is exerted on the stem 50, the junction 40 is lifted away from the urethra so that the pressure exerted on the urethra is reduced to a sufficient extent that the patient's bladder may be intentionally voided. Importantly, because the overcoat 45 of the junction 40 is encapsulated by (but not in-grown with) tissue, the junction 40 may be manipulated to a sufficient degree to allow voiding, without adversely affecting the orientation or attachment of the urethral prosthesis 10. After voiding, the tension on the stem 50 may be released to allow the junction 40 to exert pressure on a portion of the urethra to prevent subsequent unintentional bladder voiding.

The urethral prosthesis of the present invention provides several benefits. First, the prosthesis may be implanted in a variety of orientations in a patient. Second, the prosthesis may include portions that encourage tissue in-growth and portions that allow for tissue encapsulation. This may provide for some degree of movement in desired areas, such as the junction, while still maintaining sufficient attachment in the patient without requiring additional bone and/or soft tissue anchors. Third, the addition of the stem allows the patient's bladder to be voided by simply exerting tension on the stem. This may allow the prosthesis to exert a higher pressure on a portion of the patient's urethra then existing devices that do not allow for patient manipulation.

What is claimed is:

1. A urethral prosthesis comprising:
   a first arm and a second arm that are joined at proximal ends to define a junction adapted to exert pressure on a portion of a urethra when implanted, wherein the first and second arms each have a length and are capable of extending from a location below the urethra at the junction to locations in a pelvic region of a patient's body, such that distal ends of the first and second arms are capable of extending to pelvic region locations on respective right and left sides of the patient body;
   a stem joined to the junction that is adapted to decrease the pressure exerted on the portion of the urethra when a tension force is exerted on the stem, wherein the stem has a length no greater than the lengths of the first and second arms; and
   a compression member comprising a resilient pouch at the junction.

2. The urethral prosthesis of claim 1 further comprising a tensioning member associated with the first arm and a tensioning member associated with the second arm, each tensioning member being attached to the arm at a distal location and at a proximal location.

3. A urethral prosthesis comprising:
   a first arm and a second arm that are joined at proximal ends to define a junction adapted to exert pressure on a portion of a urethra when implanted, wherein the first and second arms each have a length and are capable of extending from a location below the urethra at the junction to locations in a pelvic region of a patient's body, such that distal ends of the first and second arms are capable of extending to pelvic region locations on respective right and left sides of the patient body;
   a stem joined to the junction that is adapted to decrease the pressure exerted on the portion of the urethra when a tension force is exerted on the stem, wherein the stem has a length no greater than the lengths of the first and second arms;
   a tensioning member associated with the first arm and a tensioning member associated with the second arm, each tensioning member being attached to the arm at a distal location and at a proximal location; and
   a tensioning member associated with the stem and attached to the stem at a distal location and at a proximal location.

4. The urethral prosthesis of claim 3 wherein the first and second arms comprise a mesh material.

5. The urethral prosthesis of claim 3 wherein the first and second arms comprise a coating.

6. The urethral prosthesis of claim 3 wherein the first and second arms are coated with a bioactive material.

7. The urethral prosthesis of claim 3 wherein the first and second arms comprise a silicone material.

8. The urethral prosthesis of claim 3 wherein the first and second arms have a width between about 0.5 and about 5 cm.

9. The urethral prosthesis of claim 3 wherein the first and second arms have a length of between about 5 and about 30 cm.

10. The urethral prosthesis of claim 3 wherein the stem comprises a flexible material.

11. The urethral prosthesis of claim 3 wherein the stem comprises a mesh material.

12. The urethral prosthesis of claim 3 wherein the stem further comprises a coating.

13. The urethral prosthesis of claim 3 wherein the stem is coated with a bioactive material.

14. The urethral prosthesis of claim 3 wherein the stem is joined to the junction transversely across the width of the junction.

15. The urethral prosthesis of claim 3 in combination with a guide needle.

16. The urethral prosthesis of claim 3 wherein one or more soft tissue anchor is secured to one or more distal end of the first arm and the second arm.

17. The urethral prosthesis of claim 3 wherein each of the first arm and the second arm has a length to extend from the junction, when located below a urethra, to an obturator internus muscle.

18. The urethral prosthesis of claim 3 wherein each of the first arm and the second arm has a length in a range from 15 to 25 centimeters.

19. The urethral prosthesis of claim 3 wherein the first arm and the second arm has a width in a range from 0.5 to 2.5 centimeters.

20. The urethral prosthesis of claim 3, wherein the junction has a width wider than that of the first and second arms.

* * * * *